(12) United States Patent
Borrebaeck et al.

(10) Patent No.: US 6,607,881 B1
(45) Date of Patent: Aug. 19, 2003

(54) COMBINED LIGAND AND RECEPTOR DISPLAY

(75) Inventors: Carl Borrebaeck, Hjärup (SE); Anki Malmborg, Lund (SE); Eskil Söderlind, Lund (SE)

(73) Assignee: Bioinvent International, AB, Lund (SE)

( * ) Notice: Subject to any disclaimer, the term of this patent is extended or adjusted under 35 U.S.C. 154(b) by 0 days.

(21) Appl. No.: 09/043,230

(22) PCT Filed: Sep. 13, 1996

(86) PCT No.: PCT/GB96/02271

§ 371 (c)(1),
(2), (4) Date: Jun. 30, 1998

(87) PCT Pub. No.: WO97/10330

PCT Pub. Date: Mar. 20, 1997

(30) Foreign Application Priority Data

Sep. 13, 1995 (GB) .............................................. 9503151

(51) Int. Cl.[7] .............................. C12Q 1/68; C12N 7/00; C07H 21/04

(52) U.S. Cl. .......................... 435/6; 435/7.1; 435/235.1; 435/69.1; 435/DIG. 3; 435/DIG. 23; 435/DIG. 37; 536/23.4

(58) Field of Search ........................ 435/7.1, 6, 235.1, 435/DIG. 3, DIG. 23, DIG. 37, 69.1, 69.4; 536/23.4

(56) References Cited

U.S. PATENT DOCUMENTS 5,712,089 A * 1/1998 Borrebaeck et al. ........... 435/5

FOREIGN PATENT DOCUMENTS

| EP | 0614989 | | 9/1994 |
|---|---|---|---|
| WO | WO 92/15702 | | 9/1992 |
| WO | WO 93/19172 | * | 9/1993 |
| WO | WO 9516027 | | 6/1995 |
| WO | WO 9534648 | | 12/1995 |

OTHER PUBLICATIONS

Barbas III, C.F. et al., "Assembly of combinatorial antibody libraries on phage surfaces: The gene III site"; Proc. Natl. Acad. Sci. USA, 88: 7978–7982 (1991).
Bradbury, A. et al., "Use of Living Columns to Select Specific Phage Antibodies"; Bio/Technology, 11: 1565–1568 (1993).
Charbit, A. et al., "Versatility of vector for expressing foreign polypeptides at the surface of Gram–negative bacteria"; Gene, 70: 181–189 (1988).
Dueñas, M. et al., "Clonal Selection and Amplification of Phage Displayed Antibodies by Linking Antigen Recognition and Phage Replication"; Bio/Technology, 12: 999–1002 (1994).
Francisco, J.A. et al., "Production and fluoescence–activated cell sorting of *Escherichia coli* expressing a functional antibody fragment on the external surface"; Proc. Natl. Acad. Sci. USA, 90: 10444–10448 (1993).
Fuchs, P. et al., "Targeting Recombinant Antibodies to the Surface of *Escherichia Coli*: Fusion to a Peptidoglycan Association Lipoprotein"; Bio/Technology, 9: 1369–1372 (1991).
Hawkins, R.E., et al., "Selection of Phage Antibodies by Binding Affinity Mimicking Affinity Maturation"; J. Mol. Biol., 226: 889–896 (1992).
Hedegaard, L. et al., "Type 1 fimbriae of *Escherichia coli* as carriers of heterologous antigenic sequences"; Gene, 85: 115–124 (1989).
Hofnung, M., "Expression of Foreign Polypeptides at the *Escherichia coli* Cell Surface"; Methods Cell Biol., 34: 77–105 (1991).
Huse, W.D. et al., "Generation of Large Combinatorial Library of the Immunoglobulin Repertoire in Phage Lambda"; Science, 246: 1275–1281 (1989).
Kang, A.S., et al., "Linkage of recognition and replication functions by assembling combinatorial antibody Fab libraries along phage surfaces"; Proc. Natl. Acad. Sci. USA, 88: 4363–4366 (1991).
Klauser, T. et al., "Extracellular transport of cholera toxin B subunit using Neisseria IgA protease B–domain: conformation–dependant outer membrane translocation"; The EMBO Journal, 9(6): 1991–1999 (1990).
Little, M. et al., "Surface Display of Antibodies"; Biotech. Adv., 12: 539–555 (1994).
McCafferty, J. et al., "Phage antibodies: filamentous phage displaying antibody variable domains"; Nature, 348: 552–554 (1990).
Marks, J.D. et al., "By–passing Immunization Human Antibodies from V–gene Libraries Displayed on Phage"; J. Mol. Biol., 222: 581–597 (1991).

(List continued on next page.)

*Primary Examiner*—Padmashri Ponnaluri
(74) *Attorney, Agent, or Firm*—Dann, Dorfman, Herrell and Skillman (57) ABSTRACT

A method for selecting nucleic acid sequences encoding ligand and receptor molecules capable of specific binding to each other is disclosed in which nucleic acid encoding ligand or receptor molecules is expressed in a host microorganism in combination with a surface molecule, such as *E. coli* pili, so that the ligand or receptor are displayed on the surface of the host microorganism. A replicable genetic unit, such as a filamentous bacteriophage, is used to display candidate binding partners to the ligand or receptor, with the binding of the ligand or receptor to the candidate binding partner mediating the transfer of nucleic acid from the replicable genetic unit to the microorganism. The method can be highly selective as the host microorganism is modified so that it does not display the surface molecule other than as a fusion with the ligand or receptor molecule. The method is rapid and simple and opens up new applications based on the detection of ligand and receptors where both are unknown.

14 Claims, 3 Drawing Sheets

OTHER PUBLICATIONS

Newton, G.L. et al., "*Entamoeba histolytica*: A Eukaryote Without Glutathione Metabolism"; Science, 224: 70–72 (1989).

Parmley, S.F. et al., "Antibody–selectable filamentous fd phage vectors: affinity purification of target genes"; Gene, 73: 305–318 (1988).

Pistor, S. et al., "Expression of Viral Hemagglutinin on the Surface of *E. coli*"; Klin Wochenschr, 66: 110–116 (1988).

Smith, G.P., "Filamentour Fusion Phage: Novel Expression Vectors That Display Cloned Antigens on the Virion Surface"; Science, 228: 1315–1317 (1985).

Chen, X.J. et al., "A gene fusion system using the aminoglycoside 3'–phosphotransferase gene of the kanamycin–resistance transposon Tn903: use in the yeasts *Kluyveromyces lactis* and *Saccharomyces cerevisiae*"; Gene, 69: 181–192 (1988).

\* cited by examiner-

SEQUENCE LISTING

<160> NUMBER OF SEQ ID NOS: 6

<210> SEQ ID NO 1
<211> LENGTH: 38
<212> TYPE: DNA
<213> ORGANISM: Artificial Sequence
<220> FEATURE:
<223> OTHER INFORMATION: PCR primer

<400> SEQUENCE: 1
tcacggaagc tttcatcaga ggccaacgac ggccatac                    38

<210> SEQ ID NO 2
<211> LENGTH: 52
<212> TYPE: DNA
<213> ORGANISM: Artificial Sequence
<220> FEATURE:
<223> OTHER INFORMATION: PCR Primer

<400> SEQUENCE: 2
gtcgacctgc agacagagtt attgatcatt tgatcaagtt tcctgatttt ta    52

```
<210> SEQ ID NO 3
<211> LENGTH: 83
<212> TYPE: DNA
<213> ORGANISM: Artificial Sequence
<220> FEATURE:
<223> OTHER INFORMATION: PCR Primer

<400> SEQUENCE: 3
tcacggaagc tttcatcaaa cgaaagcacg acccggacca cgctggatac ggatagattt      60
acggaggcca ccgacggcca tac                                              83

<210> SEQ ID NO 4
<211> LENGTH: 77
<212> TYPE: DNA
<213> ORGANISM: Artificial Sequence
<220> FEATURE:
<223> OTHER INFORMATION: PCR Primer

<400> SEQUENCE: 4
tcacggaagc tttcatcatc cgtacttgag ggtagtgttg tagatagtct cgttggcgag      60
gccaacgacg gccatac                                                     77

<210> SEQ ID NO 5
<211> LENGTH: 33
<212> TYPE: DNA
<213> ORGANISM: Artificial Sequence
<220> FEATURE:
<223> OTHER INFORMATION: PCR Primer

<400> SEQUENCE: 5
tcacggccat ggatgccggc cacgatgcgt ccg                                   33

<210> SEQ ID NO 6
<211> LENGTH: 35
<212> TYPE: DNA
<213> ORGANISM: Artificial Sequence
<220> FEATURE:
<223> OTHER INFORMATION: PCR Primer

<400> SEQUENCE: 6
gtccacccat ggctcatgtt tgacagctta tcata                                 35
```

COMBINED LIGAND AND RECEPTOR DISPLAY

FIELD OF THE INVENTION

The present invention relates to methods for selecting specific ligand and receptor encoding sequences and to kits for carrying out the methods.

BACKGROUND OF THE INVENTION

There is a continuing need for highly efficient selection systems in the screening of protein libraries, such as antibody libraries. Current systems are based on the display of antibodies on the surface of microorganisms containing the gene of the antibody. Specific clones can then be selected with immobilized antigens, for instance by panning on microtiter plates (Parmley and Smith, 1988, Gene, 73, 305–318 and Barbas III et al, 1991, PNAS 88, 7978–7982), selection on magnetic beads (Hawkins et al, 1992, J. Mol. Biol. 226, 889–896), immunotubes (Marks et al, 1991, J. Mol. Biol, 222, 581–597), affinity chromatography (McCafferty et al, 1990, Nature, 348, 552–554), fluorescence assisted cell sorter (FACS), antigen specific precipitation (Kang et al, 1991, PNAS, 88, 4363–4366) and SAP (Dueñas and Borrebaeck, 1994, Bio/Technology 12, 999–1002).

Several antibody libraries have been constructed on the surface of phages, e.g. a bacteriophage such as fd (McCafferty et al, 1990, Nature, 348, 552–554) or M13 (Barbas III et al, 1991, PNAS, 88, 7978–7982). The possibility of expressing antibodies (scFv) on the surface of bacteria has also been demonstrated by fusions to bacterial membrane proteins like Lpp-Omp A (Francisco et al, 1993, PNAS, 90, 10444–10448) and PAL (Fuchs et al, 1991, Bio/Technology, 9, 1369–1372). For a recent review of antibody display systems and the screening of antibody libraries, see Little, 1994, Biotech. Adv., 12, 539–555.

Antigen libraries have been constructed following essentially the same principles as antibody libraries, e.g. peptide libraries on the surface of bacteriophages (Smith, 1985, Science, 228, 1315–1317). Expression of antigens on the surface of bacteria has been demonstrated by fusions to LamB (Charbit et al, 1988, Gene, 70, 181–189 and Bradbury et al, 1993, Bio/Technology, 1565–1568), Omp A (Pistor and Hoborn, 1989, Klin. Wochenschr., 66, 110–116), fimbriae (Hedegaard and Klemm, 1989, Gene, 85, 115–124 and Hofnung, 1991, Methods Cell Biol., 34, 77–105), IgA protease β domain (Klauser et al, 1990, EMBO J., 9, 1991–1999) and flagellae (Newton et al, 1989, Science, 244, 70–72).

However, many of the prior art selection steps, such as panning and affinity chromatography, are not very efficient, and even if the yield of antibody or antigen is reasonable, these techniques do not provide any information about the nucleic acid sequence encoding it.

SUMMARY OF THE INVENTION

In the past, it has not been possible to combine a ligand library with a receptor library in order not only to clone and select one of the specific binding pair members and their corresponding nucleic acid sequences encoding them, but actually both.

The present invention provides an efficient screening technique to obtain corresponding ligand/receptor molecules and establishes a physical and logical connection between the two and their encoding sequences. This has the advantage that it is simple and rapid and opens up possibilities of applications, such as detecting new ligands and/or receptors, where both are unknown, as well as improvements regarding epitope mapping, localization of gene products and drug design.

Accordingly, in one aspect, the present invention provides a method for selecting nucleic acid sequences encoding ligand and receptor molecules capable of specific binding to each other, the method comprising:

(a) expressing in a host microorganism nucleic acid encoding a surface molecule which is operably linked to the expression of nucleic acid encoding a ligand or receptor molecule, or functional fragments thereof, so that the microorganism expresses the surface molecule and the ligand or receptor molecule as a fusion and displays it on its surface, wherein the host microorganism is modified so that it does not display the surface molecule other than as a fusion with the ligand or receptor molecule;

(b) contacting the modified host microorganism of step (a) with one or more replicable genetic units capable of expressing nucleic acid encoding ligand or receptor molecules, or functional fragments thereof, the ligand or receptor molecules being candidates for specific binding to the molecules displayed by the host microorganisms of step (a) and being expressed as fusions with a surface protein of the replicable genetic unit, wherein binding of the surface displayed ligand and receptor molecules mediates the transfer of the nucleic acid encoding the ligand or receptor from the replicable genetic unit to the microorganism; and, (c) selecting the host microorganisms containing the nucleic acid sequences encoding the ligand and receptor molecules, or functional fragments thereof.

Thus, in this aspect, the invention provides a method for selecting nucleic acid sequences encoding ligand and receptor molecules, the selection arising from modification to the host microorganism so that infection or transfer of the nucleic acid from the replicable genetic unit takes place when binding of the receptor and ligand molecules occurs. Thus, infection via the normal route, e.g. for *E. coli* via wild type pili, is prevented by a modification to the host microorganism to prevent the display of a given type of surface molecule so that the only surface molecules of that type that are displayed are those fused to the receptor or ligand.

In a preferred aspect, the host microorganism expresses and displays modified ligand molecules, with the replicable genetic units expressing the candidate receptor molecules. Thus, this provides a method for selecting specific ligand and receptor encoding sequences wherein:

(a) the expression of a surface molecule encoding sequence is combined with a ligand encoding sequence, or a sequence encoding a functional fragment thereof, so that the host microorganism expresses modified ligand molecules on its surface;

(b) infecting, or in other ways transferring DNA to, the modified host organism of step (a) with a genetically modified replicable genetic unit capable of expressing a receptor, or a functional fragment thereof, fused to a surface protein of the replicable genetic unit; and, (c) selecting infected host organisms containing specific ligand and receptor encoding sequences or sequences encoding functional fragments thereof.

In the above aspects, the method of the invention optionally includes the additional step of:

(d) isolating the nucleic acid sequences encoding the ligand or receptor molecules.

Conveniently, the isolation can be achieved by associating different selection markers (e.g. different antibiotic resistance markers) with the nucleic acid sequences encoding the ligand and receptor molecules. Thus, the host microorganisms containing nucleic acid sequences encoding a specific binding pair can be selected by growing them in the presence of both antibiotics. After this, the vectors containing nucleic acid encoding the ligand and the receptor can be separated from each other by omitting one of the antibiotics from the growing medium.

In different embodiments, this method can be used to screen:

(a) microorganisms displaying one type of ligand or receptor molecule against libraries of replicable genetic units displaying different receptor or ligand molecules;

(b) libraries of microorganisms displaying different ligand or receptor molecules against replicable genetic units displaying one type of receptor or ligand molecule; or, (c) libraries of microorganisms displaying different ligand or receptor molecules against libraries of replicable genetic units displaying different receptor or ligand molecules.

In the above aspects, the host microorganisms do not express the normal (wild type) surface molecules that are used to display ligand or receptor molecules as fusions on its surface. This means that the replicable genetic units used to display candidate binding partners of the ligand or receptor molecule will only infect the microorganisms when binding between the ligand or receptor and a binding partner takes place, i.e. infection via the normal surface molecule of the microorganism is not possible as they are not displayed.

Thus, in one embodiment, the host microorganism is an *E. coli* strain in which the F episome is mutated in the traA gene that builds up pilin molecules, but which contains the other genes required for infection by bacteriophages, e.g. traL, traE, traY etc. Accordingly, these strains of *E. coli* are F$^-$, that is they do not produce functional pili, except when transformed with vectors comprising nucleic acid encoding fusions of the pilin and the ligand or receptor molecules. This allows wild type bacteriophages (e.g. M13, fd etc) displaying the candidate binding partners attached to a phage surface protein (e.g. pIII or pVIII protein) to be used, as the bacteriophage will only selectively infect those *E. coli* cells binding to the phage via the specific interaction of the binding partners. As the *E. coli* do not have wild type pili, this prevents the bacteriophage from infecting the *E. coli* unselectively. Thus, the present invention does not rely on engineering the replicable genetic units to limit their infectivity, and so obtain selectivity of DNA transfer, helping to avoid the difficulties that can be encountered in generating large libraries with deleted bacteriophages, such as pIII deleted M13 phage.

In embodiments of the invention that use the pili of the microorganism to display the ligand or receptor molecules, surprisingly good selectivity is obtained when the ligand or receptor nucleic acid is expressed as a fusion at the carboxy terminus of the pili.

Preferably, the vectors comprising the nucleic acid encoding the ligand and receptor molecules have different origins of replication (pME1, p15A, PSC101) so that both vectors can be stably maintained when transferred to the host microorganism.

In the method, steps (a) and (b) can be simultaneous or sequential. However, conveniently, the host microorganism will be cultured so that they display the ligand or receptor molecules, prior to infection with the replicable genetic units.

Accordingly, the present invention provides a method for selection of nucleic acid sequences encoding ligand and receptor molecules capable of specific binding to each other. The designed system enables the passage of DNA over cell membranes and is denoted "Cellular Linkage of ligand-receptor Affinity Pairs" (CLAP). The DNA which is translocated from the replicable genetic unit over the cell membrane is denoted "membrane passage DNA" (mp-DNA) and this genetic information outside the cell can be defined, constructed, designed and developed using recombinant DNA technology. The type of specific DNA, which is translocated over the cell membrane, is determined by the genetic information, DNA, inside the cell. This genetic information inside the cell can be defined, constructed, designed and developed using recombinant DNA technology and is denoted "translocation determining DNA" (td-DNA). Thus, in a preferred embodiment, this selectivity of DNA transfer is achieved using a strain of *E. coli* that have a mutation in the F episome so that they do not display functional pili. This means that when they are transformed with a vector comprising nucleic acid encoding a ligand or receptor for expression as a fusion with the pili, only these modified pili are displayed on the *E. coli* surface.

Based on the capability of specific td-DNA to determine the specific type of mp-DNA which is to be translocated into cells, the CLAP system can be used to construct a genetic library of td-DNA to determine the translocation of specific mp-DNA from a genetic library of mp-DNA. Thus, it is possible, in one single reaction, to mix a replicable genetic unit or units which encode genetic library/libraries of td-DNA and a genetic library/libraries of mp-DNA and these libraries encode proteins/peptides which are expressed from the genetic library/libraries. The individual td-DNA in individual cells will determine the translocation of individual mp-DNA into each cell.

Thus, the corresponding pairs of td-DNA and mp-DNA will be linked in the same cell. Individual td-DNA and mp-DNA can be separated and isolated using selection markers and therefore both the td-DNA and mp-DNA from the same cell can be separated, analyzed, defined, redesigned and reconstructed. The possibility to screen two gene libraries against each other in one reaction step allows the selection of ligand-receptor pairs without information of the individual clones building up the ligand-receptor pair. The td-DNA can be constituted of genes encoding proteins or peptides of various sizes. Individual cells encode specific proteins/peptides defined by the td-DNA in the cell and this protein or peptide is exposed on the cell surface. These exposed proteins/peptides can be constructed as mp-DNA and displayed on the surface of a replicable genetic unit. These proteins/peptides can be viewed as receptors and can then interact with ligand molecules exposed, encoded by the td-DNA, on the cell surface. When such interactions occur the ligand-receptor interaction mediates the passage of receptor DNA (mp-DNA) into the cell.

In one embodiment, the molecules on the cell surface are receptors and the molecules on the replicable genetic unit are ligands. A td-DNA can consist of a cDNA-library and the mp-DNA can consist of an antibody fragment gene library, where antibody fragment specificities can be selected against different protein/peptides ligand. The td-DNA can also consist of DNA encoding one type of peptide which can bind biotin and biotinylated chemical compounds. The biotin-peptide interaction allows the immobilization of biotinylated chemical compounds on the cell surface and these immobilized compounds can function as ligands/receptors for determining the translocation of mp-DNA encoding receptors/ligands. Antibody fragments with affinity to the immobilized chemical compound can be selected from a genetic library encoding different antibody specificities/affinities. The mp-DNA encoding the specificity/affinity of the selected antibody fragment is then replicated inside the cell, which displayed the biotin binding peptide binding to the biotinylated chemical compound. Other types of modifications of the chemical compounds can be used, which bind the biotin binding peptide and other types of peptides can be displayed on the cell surface which bind the modified chemical compound.

In a further aspect, the present invention provides a kit containing vectors for use in the methods described herein.

In this aspect, a preferred kit comprises:
(a) a host microorganism modified so that it does not display a wild type surface protein;
(b) a vector encoding said surface protein and having restriction sites for the insertion of nucleic acid encoding ligand or receptor molecules, or functional fragments thereof, so that when transformed into the host microorganism, the surface molecule and the ligand or receptor molecule are expressed as a fusion and displayed on the surface of the microorganism;
(c) a bacteriophage having a site for insertion of nucleic acid encoding candidate binding partners to the ligand or receptor so that the binding partners are expressed displayed on the surface of the bacteriophage as a fusion with a surface protein of the bacteriophage.

The above method can be used in a variety of applications, inter alia:

(1) cDNA libraries derived from, e.g. genome sequences, human or other tissue, can be cloned into the fusion vector and subsequently transfected into the microorganism host. Thus, by the way of expressing cDNA derived molecules as fusion proteins to pilin, we can use these cells as expressors of ligands. Subsequently, bacteriophages displaying antibody fragments derived from immunised or naive B cells from human or other origin will be formed and allowed to interact with the host microorganism expressing cDNA derived molecules. The infection event takes place and is mediated only by specific receptor-ligand interactions found between microorganisms and bacteriophages. The genetic information for each ligand and receptor pair can then be isolated.

(2) cDNA libraries derived from cancer patients and differentially PCR selected against normal tissue can be bacterially displayed, as described above. In the same manner, antibody libraries displayed on bacteriophages, derived from normal patients or cancer patients, are allowed to interact with the cDNA displaying microorganisms and infection is again mediated by specific receptor-ligand interactions.

(3) cDNA derived from allergen encoding gene sequences can be bacterially displayed as described above. In the same manner, antibody libraries displayed on bacteriophages derived from normal or atopic patients are allowed to interact with the cDNA displaying microorganisms and infection is again mediated by specific receptor-ligand interactions.

DETAILED DESCRIPTION

Definitions

As used herein "library" means a number of fragments of a ligand or receptor population, either their encoding sequences or their corresponding protein or peptide sequence displayed on a surface. Typically, libraries will comprise a substantial number of such nucleic acid sequences or peptides. By way of example, libraries can be constructed after the principles outlined by Huse et al, 1989, Science, 246, 1275.

The expressions "ligand" and "receptor" refer to pairs of molecules or functional parts thereof, capable of specific binding to each other. Examples of such specific ligand-receptor pairs are: antibody-antigen, hormone-hormone receptor, growth factor-growth factor receptor, enzyme-substrate and biotin-avidin etc.

"Host microorganisms" include bacteria such as *E. coli* or other Gram negative bacteria, Gram positive bacteria, as well as unicellular microorganisms of eukaryotic origin such as yeast.

"Replicable genetic unit" comprises viruses and bacteriophages such as M13, fl and fd, but also bacteria, as well as unicellular microorganisms of eukaryote origin such as yeast.

"Membrane passage DNA (mp-DNA)" are nucleic acid sequences encoding ligand or receptor molecules, or functional fragments thereof, this nucleic acid being initially contained in a replicable genetic unit and being transferred to the host microorganism if binding of the displayed ligand/receptor pair takes place.

"Translocating determining DNA (td-DNA)" are nucleic acid sequences encoding ligand or receptor molecules, or functional fragments thereof, this nucleic acid being contained in a host microorganism and associated with sequences that mediate transfer of mp-DNA from a replicable genetic unit when displayed ligand and receptor molecules bind to each other.

The "surface molecule" will be dependent on the choice of host microorganism and replicable genetic unit. If the host organism is *E. coli*, suitable surface molecules can be selected from the group OmpA, lipoprotein, Lpp, IgA protease, LamB, fimbriae, flagellae or pilin. Pilin is preferred. Dependent on the choice of the replicable genetic unit, the surface molecule can be any surface molecule involved in the infection of, or in the transformation of DNA to, the host. Preferred replicable genetic units are filamentous bacteriophages such as fd and M13, suitable surface molecules of these phages can be protein III or protein VIII. Most preferred is protein III of the filamentous bacteriophage M13.

The "selection" of host organisms which have been infected, or otherwise transformed with DNA, is dependent on the fact that only host organism and replicable genetic unit pairs which have formed a receptor-ligand pair will infect each other.

Host organisms which have been infected, or in other ways transformed with DNA, can be "isolated" by the use of different selection markers which confer different antibiotic resistance, e.g. ampicillin, tetracycline or chloramphenicol, on different types of DNA.

"Determination" of the encoding sequences can be conducted with conventional DNA (or RNA) manual or automatic sequencer, according to known methods.

"Encoding sequence" can mean the corresponding DNA sequence of a protein or RNA or complementary DNA or RNA sequence thereof.

With "protein" means any sequence of amino acids including any peptide fragments thereof.

EXAMPLES

The following examples are provided by way of illustration and are not intended to limit the scope of the invention. Those skilled in the art will be aware of alternative routine procedures that could be substituted for those described in the examples below.

Example 1

Vector Constructions (a) A vector (pTRAPchl$^R$) carrying the information for the pili molecule, pilin, of *E. coli* was constructed. The traA gene, encoding the pilin, was amplified by PCR from the plasmid pBF203 using:
5'-TCA CGG AAG CTT TCA TCA GAG GCC AAC GAC GGC CAT AC, (SEQ ID NO:1) as the 3' primer; and,
5'-GTC GAC CTG CAG ACA GAG TTA TTG ATC ATT TGA TCA AGT TTC CTG ATT TTT A (SEQ ID NO:2) as the 5' primer.

The amplified fragment was cut with restriction enzymes Hind III/Pst I, purified and inserted into the Hind III/Pst I site of the plasmid pAM18chl$^R$. The new vector was called pTRAPchl$^R$ and formed functional pili when co-transformed with an F episome called JCFLtraA1, which has a point mutation in the traA gene (see Achtman et al, J. Bacteriol., 106, 529–538, (1971)). The mutated episome contains all of the genes other than traA needed for the infection procedure, the traA being responsible for building up the pilin molecules.

pAMI8chl$^R$ vector was constructed by isolating the Hae II lacZ α peptide fragment from pUC18, treating with S1 nuclease and ligating into the "filled-in" Hind III/BamH I site of PACYC 184.

(b) A vector (pTRAPV3chl$^R$ was constructed that included nucleic acid encoding the pilin molecule, with an addition of nucleic acid sequence encoding a part of the V3 loop of HIV-1 (V3 is the variable loop of gp120 of HIV-1 (LA1)). The nucleic acid encoding the V3 loop was arranged so that it would be expressed at the C-terminal end of the pilin molecule. This was achieved through PCR amplification of the traA gene from the plasmid pBF203, with a 5' primer as described above, and the following 3' primer:
5'-TCA CGG AAG CTT TCA TCA AAC GAA AGC ACG ACC CGG ACC ACG CTG GAT ACG GAT AGA TTT ACG GAG GCC ACC GAC GGC CAT AC (SEQ ID NO:3),
which includes 45 bases coding for 15 amino acids of the V3 loop. This amplified fragment was inserted, as described above, in pAM18chl$^R$. This vector was called pTRAPV3chl$^R$.

(c) A vector (pTRAPCMVchl$^R$) was constructed that carries nucleic acid encoding a pilin molecule with the addition of the sequence of a part of the gB protein of CMV (cytomegalovirus). The nucleic acid encoding the gB fragment was arranged so that it would be expressed at the C-terminal end of the pilin molecule. This was achieved through PCR amplification of the traA gene from the plasmid pBF203 with a 5' primer as described above, with the following 3' primer:
5'-TCA CGG AAG CTT TCA TCA TCC GTA CTT GAG GGT AGT GTT TA GAT AGT CTC GTT GGC GAG GCC AAC GAC GGC CAT AC (SEQ ID NO:4),
which includs 39 bases coding for 13 amino acids of the gB protein. This amplified fragment was inserted in pAM18chl$^R$ as described above. This vector was called pTRAPCM-Vchl$^R$.

Example 2

Vector Construction

Construction of vectors containing nucleic acid encoding antigen fragments.

(a) A vector (PTRAPtet$^R$) carrying the information for the pili molecule, pilin, of *E. coli* was contructed. The traA gene, encoding the pilin, was amplified by PCR from the vector pTRAPchl$^R$ (example 1) using:
5'-TCA CGG CCA TGG ATG CCG GCC ACG ATG CGT CCG (SEQ ID NO:5) as 3' primer; and,
5'-GTC CAC CCA TGG CTC ATG TTT GAC AGC TTA TCA TC (SEQ ID NO:6) as 5' primer.

The amplified fragment was cut with restriction enzyme NcoI, purified and inserted into the NcoI site of the plasmid pACYC184ΔHindIII. The new vector was called pTRAPtet$^R$ and was capable of forming functional pili if co-transformed with an F episome called pOX38A::CAT, which has a CAT cassette inserted into its traA gene to abolish its function.

pACYC184ΔHindIII was constructed by cutting the plasmid pACYC184 with HindIII, treatment with Klenow and religation, to abolish the unique HindIII site.

(b) A vector (pTRAPV3tet$^R$) was constructed that carries the information for the pilin molecule with an addition of the sequence of a part of the V3 loop of HIV-1 (V3 is the variable loop of gp120 of HIV-1 (LA1)) constructed to be expressed in the C-terminal end of the pilin molecule.

This was achieved through PCR amplification of the traA gene and the V3 peptide-coding sequence from the vector pTRAPV3chl$^R$, with the primers described in example 2a. This amplified fragment was inserted, as described above, in pACYC184ΔHindIII. This vector is called pTRAPV3tet$^R$.

(c) A vector (pTRAPCMVtet$^R$) was constructed that carries the information for the pilin molecule with an addition of the sequence of a part of the gB protein of CMV (cytomegalovirus), constructed to be expressed in the C-terminal end of the pilin molecule. This was achieved through PCR amplification of the traA gene and the CMV peptide-coding sequence from the vector pTRAPCMVchl$^R$, with the primers described in example 2a. This amplified fragment was inserted, as described above, in pACYC184ΔHindIII. This vector was called pTRAPCM-Vtet$^R$.

(d) A vector (pAM18tet$^R$) was constructed by PCR amplification of the pUC-insert from pAM18chl$^R$, containing a lacZ α peptide fragment, using primers as described in example 2a. This amplified fragment was inserted, as described above, in pACYC184ΔHindIII. This vector was called pAM18tet$^R$.

*E. coli* strain TG1 was used for the genetic constructions.

Example 3

Construction of Filamentous Bacteriophages Displaying Antibody Fragments

The filamentous bacteriophage VCS M13 (helper phage) was obtained from Stratagene.

The M13 phages expressing Fab against the V3 loop of HIV (anti-V3), Fab against phenyl-oxazolone (anti-ox), Fab against hen egg lysozyme (anti-lys) and scFv against gB of CMV (anti-CMV), respectively, were prepared as follows: XL1 Blue *E. coli* strain cells were transformed (according to Hanahan, 1983, J. Mol. Biol. 166, 557–580) with the vector pEXmide III (Söderlind et al, 1993, Bio/Technology 11, 503–507) carrying the VH and VL sequences of anti-V3, anti-ox and anti-lys, respectively, or with the vector pEXmide 4 (Ohlin, M., Owman, H., Mach, M. and Borrebaeck, C. A. K., 1996, "Light chain shuffling of a high affinity antibody results in a drift in epitope recognition.", Mol. Immunol., 33, 47–56, (1996)) carrying the VH and VL sequences for anti-CMV, and grown in ampicillin, tetracycline and glucose containing LB media overnight at 37° C. The bacteria was reinoculated and grown to OD (600 nm) of 0.5, washed with LB and resuspended in LB, containing ampicillin and tetracycline, and then superinfected with VCS M13 in the ratio 20 phages/cell. After growth for 1 hour at 37° C. kanamycin was added and growth was continued overnight. The phage containing supernatant was recovered by centrifugation 8000 rpm for 10 minutes.

The phages obtained carry the antibody Fab fragments linked by the heavy chain constant domain to the N-terminal of protein III (pIII) or the antibody scFv fragments linked by the light chain variable domain to the N-terminal of pIII.

Example 4

Infection Assays

To prove the function of the above mentioned genetic constructions three types of *E. coli* cells were established; (a) *E. coli* strain JC 3272, containing the unmutated F episome (JCFLO) (b) *E. coli* strain ED 2601, containing the F episome mutated in the traA gene (JCFLtraA1) and transformed with the pTRAP vector and (c) *E. coli* strain ED 2601, containing the F episome mutated in the traA gene (JCFLtraA1) and transformed with the pTRAPCMV vector.

The function of each type of *E. coli* was evaluated through its ability to express functional F pili and thus be infected with filamentous bacteriophages.

Infections assays were carried out by incubating 100 μl of *E. coli* with 10 μl of phage stock at room temperature for 45 minutes, followed by plating on LB agar plates with the appropriate antibiotics (kanamycin for the helper phages and ampicillin for the specific phages, and chloramphenicol for the pTRAP constructs). The number of colony forming units, cfu, per plate were counted after overnight incubation in 37° C.

Figure 1:
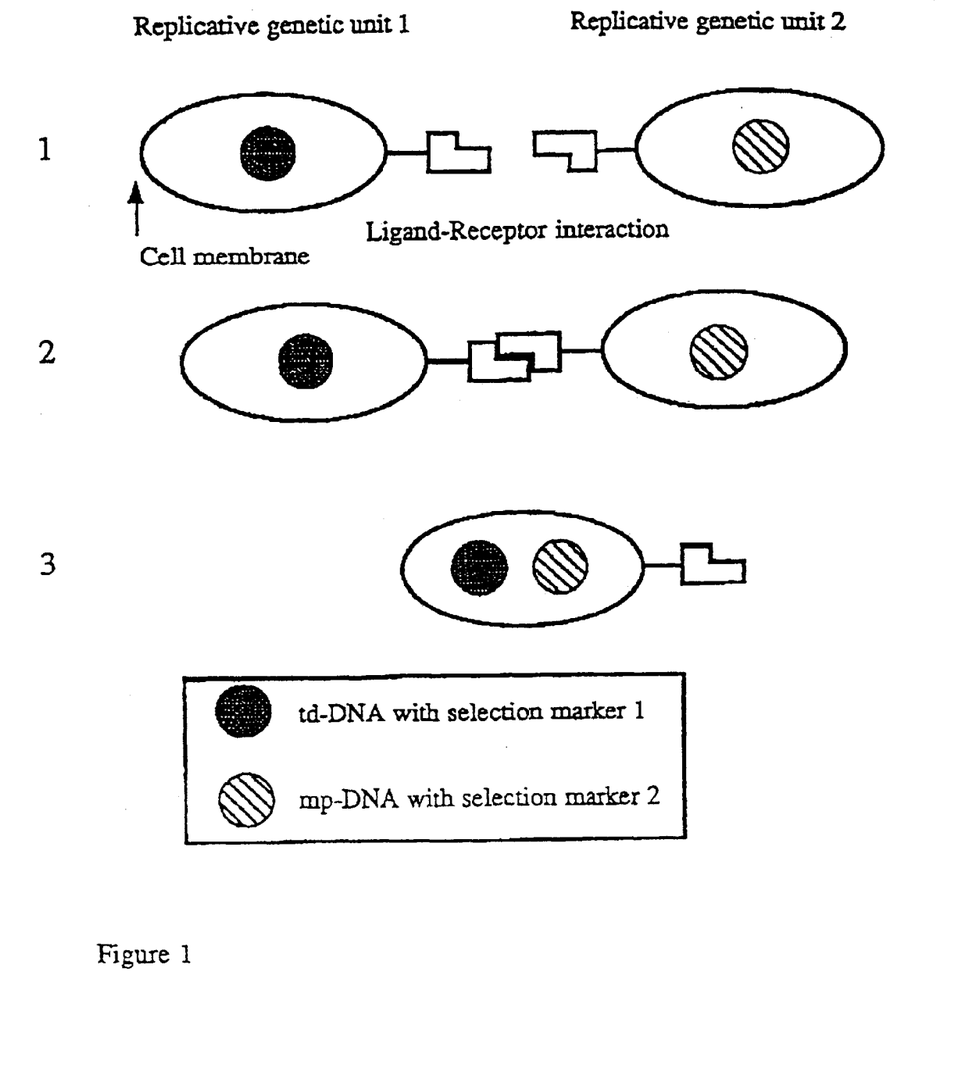
FIG. 1 shows a schematic illustration of the CLAP infection.
Figure 2:
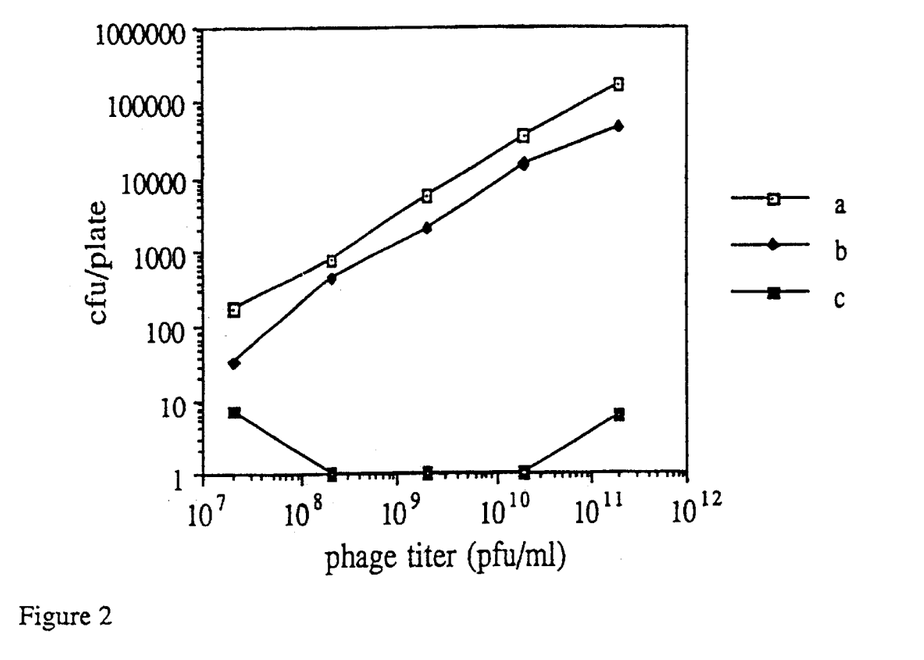
FIG. 2 shows the infectivity by VCS M13 helper phages of *E. coli* carrying the plasmids (a) JFLO, (b) PTPAP and JCFLtraA1 and (c) pTRAPCMV and JCFLtraA1.
Figure 3:
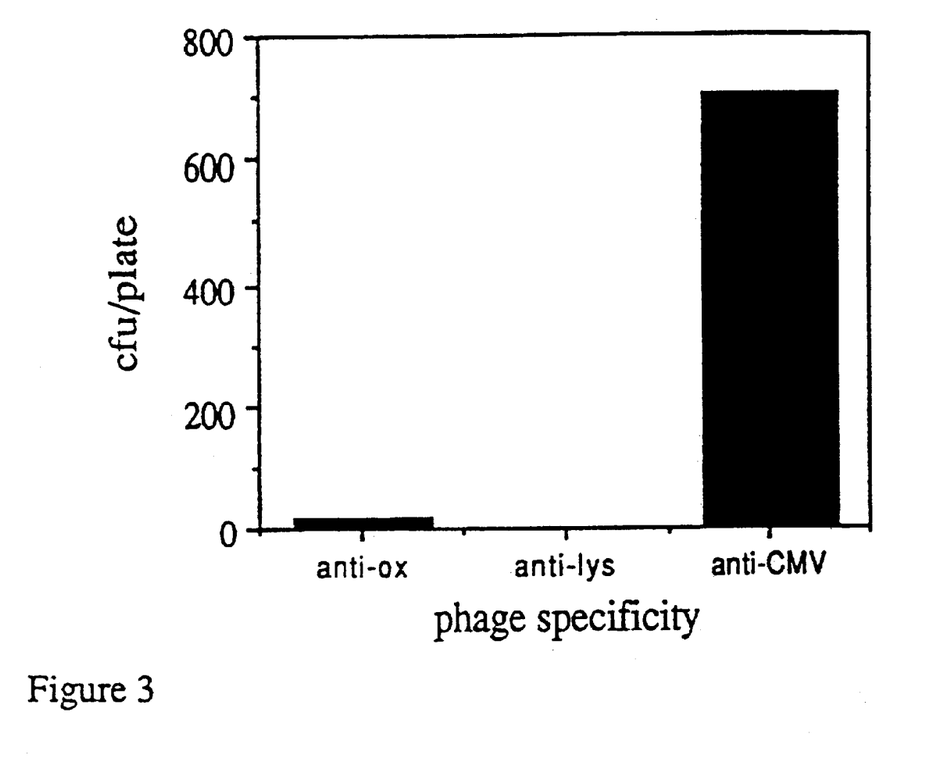
FIG. 3 shows the infectivity of *E. coli* carrying the plasmids pTRAPCMV and JCFtraA1 by a specific phage stock (anti-CMV) and two non-specific phage stocks (anti-lys and anti-ox).

The results are given in FIGS. 2 and 3. FIG. 2(*a*) shows that the wild type of VCS M13 expressing the pIII on the surface infects the F episome, JCFLO, containing *E. coli*. In 2(*b*) *E coli* containing the F episome mutated in the traA gene, JCFLtraA1, and co-transformed with the pTRAP vector is infected by the VCS M13. This construct thus led to the formation of functional F pili, whereas the co-transformation with pTRAPCMV in FIG. 2(*c*) completely blocked with infection of wild type VCS M13 phage. Thus, a comparison of FIGS. 2(*a*) and (*b*) shows that the number of cfu obtained using the constructs of the invention (FIG. 2(*b*)) was comparable to the wt situation (FIG. 2(*a*)).

FIG. 3 shows the specificity of the infection. *E. coli* containing mutated F episome, JCFLtraA1, co-transformed with pTRAPCMV, form pili carrying the 13 amino acids peptide of gB of CMV. The anti-ox and anti-lys containing phages, expressing the anti-phenyl oxazolone or the anti-lysozyme antibody fragments connected to the pIII surface, did not infect the host carrying the gB of CMV on the pili due to lack of specificity. The antigen specific infection, mediated by 13 amino acid peptide of gB on the pilin molecule, was clearly demonstrated by anti-CMV phages, which gave>700 cfu/plate. Thus, inside the *E. coli* cells the two plasmids encoding gB peptide (ligand) and anti-CMV scFv (receptor) were physically linked by the boundaries of the cell membrane.

The references mentioned above are all incorporated by reference.

What is claimed is:

1. A method for selecting nucleic acid sequences encoding specific binding pairs comprising a first member and a second member, having specific binding affinity for each other, the method comprising:

(a) providing a host microorganism which has been modified to prevent display of a surface molecule;

(b) expressing in said host microorganism a nucleic acid encoding said surface molecule which is operably linked to a nucleic acid encoding a first member of said specific binding pair, said nucleic acid further encoding a first selectable marker which confers resistance to a first selection compound, wherein said first member is an antibody or functional fragment thereof having a specific binding property of said antibody, expression of said nucleic acid in said host microorganism resulting in the production of a first fusion protein comprising said surface molecule and said first member of said specific binding pair displayed on the surface of said host microorganism;

(c) contacting the host microorganism of step (b) with at least one replicable genetic unit which expresses a nucleic acid encoding a second member of said specific binding pair, wherein said second member is an antigen, operably linked to a nucleic acid encoding a surface protein of said replicable genetic unit, said nucleic acid further encoding a second selectable marker which confers resistance to a second selection compound, expression of said nucleic acid in said replicable genetic unit resulting in the production of a second fusion protein displayed on the surface of said replicable genetic unit, said displayed second fusion protein comprising said second member of said specific binding pair produced by said replicable genetic unit having specific binding affinity for said first fusion protein displayed on the surface of host microorganisms of step (b), said contact of said displayed first and second binding pair members effectuating infection of said host microorganism by said replicable genetic unit, thereby transferring said nucleic acid of said replicable genetic unit into the host organism;

(d) selecting infected host microorganisms containing both nucleic acids encoding said first and second specific binding pair members which grow in the presence of said first and second selection compounds; and (e) optionally, isolating said nucleic acids encoding said first and second binding pair members from said host microorganisms.

2. The method of claim 1 wherein a library of host microorganisms displaying different first members of a specific binding pair is contacted with libraries of replicable genetic units displaying candidate second specific binding pair members thereby simultaneously screening both libraries for said specific binding pair members.

3. The method of claim 1, wherein the host microorganism is modified prior to contact with the replicatable genetic unit of step (b) to display a specific binding pair member by a bacterial display vector.

4. The method of claim 1 wherein the host microorganism is the bacteria *E. coli*.

5. The method of claim 1 wherein the surface molecule of the host organism is selected from the group consisting of, OmpA, IgA protease and pilin.

6. The method of claim 5 wherein the surface molecule is pilin.

7. The method of claim 1 wherein the replicable genetic unit is a phage display vector.

8. The method of claim 7, wherein the phage display vector is a filamentous bacteriophage.

9. The method of claim 8 wherein the filamentous bacteriophage is selected from the group consisting of fd, fl, and M13.

10. The method of claim 1 wherein the surface protein of the replicable genetic unit is pIII.

11. A kit for use in a method for selecting nucleic acid sequences encoding specific binding pair members, the kit comprising:

(a) a host microorganism modified to prevent display of a wild type surface protein;

(b) a vector encoding said surface protein and having restriction sites for the insertion of nucleic acid encoding a first member of said specific binding pair, wherein said first member is an antibody or functional fragment thereof having a specific binding property of said antibody, transformation of said host microorganism with said vector resulting in expression of a first fusion protein comprising said surface molecule and said first specific binding pair member being displayed on the surface of said host microorganism;

(c) a bacteriophage having a site for insertion of a nucleic acid molecule encoding a second member of said specific binding pair, wherein said second member is an antigen, said nucleic acid molecule being inserted into a nucleic acid encoding a surface protein of said bacteriophage, expression of said nucleic acid resulting in production of a fusion protein displayed on the surface of said bacteriophage, binding of said specific binding members on said host microorganism and said bacteriophage resulting in infection of said host microorganism by said bacteriophage;

(d) optionally, selection agents for isolating host microorganisms comprising nucleic acids encoding both first and second binding pair members; and (e) optionally reagents for isolating said nucleic acids encoding said first and second specific binding pair members.

12. The method of claim 1, wherein the nucleic acid sequence of a first specific binding pair member is operably linked to a first selection marker and a second specific binding pair member is operably linked to a second selection marker.

13. The kit of claim 11 wherein the surface molecule of the host organism is selected from the group consisting of OmpA, IgA protease and pilin.

14. The method of claim 1 wherein functional fragments of said antibody are selected from the group consisting of Fab and scFv fragments.

* * * * *